(12) United States Patent
Cozzi et al.

(10) Patent No.: US 8,610,111 B2
(45) Date of Patent: Dec. 17, 2013

(54) BISTABLE CARBAZOLE COMPOUNDS

(75) Inventors: Pier Giorgio Cozzi, Bologna (IT); Luca Zoli, Bologna (IT); Alessandro Paolo Bramanti, Lecce (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 462 days.

(21) Appl. No.: 13/043,942

(22) Filed: Mar. 9, 2011

(65) Prior Publication Data

US 2011/0155996 A1 Jun. 30, 2011

Related U.S. Application Data

(63) Continuation-in-part of application No. PCT/EP2009/006594, filed on Sep. 10, 2009.

(30) Foreign Application Priority Data

Sep. 10, 2008 (IT) ................ MI2008A1613

(51) Int. Cl.
*H01L 29/15* (2006.01)
*H01L 35/24* (2006.01)
*H01L 51/00* (2006.01)

(52) U.S. Cl.
USPC ................................ 257/40; 257/9

(58) Field of Classification Search
USPC ............... 257/9–17, 40, E29.072
See application file for complete search history.

(56) References Cited

U.S. PATENT DOCUMENTS

| | | | |
|---|---|---|---|
| 6,333,516 B1* | 12/2001 | Katoh et al. | 257/22 |
| 8,076,668 B2* | 12/2011 | Wolkow et al. | 257/40 |
| 8,148,715 B2* | 4/2012 | Hollenberg et al. | 257/14 |
| 8,278,654 B2* | 10/2012 | Wolkow et al. | 257/40 |

OTHER PUBLICATIONS

Jiao et al., "Building Blocks for the Molecular Expression of Quantum Cellular Automata. Isolation and Characterization of a Covalently Bonded Square Array of Two Ferrocenium and Two Ferrocene Complexes," *J. Am. Chem. Soc. 125*:7522-7523, 2003.
Lent et al., "Molecular Quantum-Dot Cellular Automata," *J. Am. Chem. Soc. 125*:1056-1063, 2003.
Lu et al., "Theoretical Study of Molecular Quantum-Dot Cellular Automata," *Journal of Computational Electronics 4*:115-118, 2005.

(Continued)

*Primary Examiner* — Cuong Q Nguyen
(74) *Attorney, Agent, or Firm* — Seed IP Law Group PLLC

(57) ABSTRACT

Bistable carbazole compounds of formula (I)

(I)

are described, wherein M is Fe, Co, Ru or Os, preferably Fe, useful as basic functional units for computing systems based on the QCA (Quantum Cellular Automata) paradigm; a process for their preparation is also described.

20 Claims, 1 Drawing Sheet

(56) References Cited

OTHER PUBLICATIONS

Qi et al., "Molecular Quantum Cellular Automata Cells. Electric Field Driven Switching of a Silicon Surface Bound Array of Vertically Oriented Two-Dot Molecular Quantum Cellular Automata," *J. Am. Chem. Soc.* 125:15250-15259, 2003.

Wang et al., "Synthesis, crystal structure, electrochemical properties and large optical limiting effect of a novel 3-(E)-ferrocenyl-vinyl-*N*-hexyl carbazole," *Transition Metal Chemistry* 32:551-557, 2007.

\* cited by examiner

BISTABLE CARBAZOLE COMPOUNDS

BACKGROUND

1. Technical Field

The present disclosure regards the field of chemical and electronic industry. In particular, the disclosure regards new carbazole derivatives bearing metallocene alkyl substituents on the benzene rings and their use as basic functional units for computing systems based on the QCA (Quantum Cellular Automata) paradigm.

2. Description of the Related Art

The QCA paradigm was elaborated in the '90s at the University of Notre Dame, Illinois, by C. S. Lent and collaborators (see, C. S. Lent, P. Douglas Tougaw, W. Porod, G. H. Bernstein, *Nanotechnology* 1993, 4, 49) and represents a transistor-less alternative to current computers, adapted for downscaling size and a power consumption beyond Moore's law.

According to the QCA paradigm, the fundamental computational unit (cell) is an arrangement of four quantum dots at the corners of a square, with possibly a fifth dot at the center. The dots are charged with two electrons with opposite spin, capable of tunneling between dots of the cell but not outside the cell.

The electrons are normally localized along a diagonal of the cell, in order to minimize internal repulsion, and the diagonals thus code the two stable states for binary logic and arithmetic. The choice of the diagonal will depend on the energy of the ground state of the single dots, which in turn depends on the arrangement of the electrons inside the surrounding cells (especially those in the neighborhood). Therefore, electrostatic interaction is the driving force for making the different cells work together: when the charge configuration inside a cell changes, the neighboring cell will consequently change, while the electrons move around the dots of the cell and resettle onto the new minimal energy configuration.

The use of bistable molecules in computing systems based on the QCA paradigm was described in various studies, including J. Jiao, G. J. Long, F. Grandjean, A. M. Beatty, T. P. Fehlner, *J. Am. Chem. Soc.* 2003, 125, 7522; Y. Lu, C. S. Lent, *J. Comput. Elec.* 2005, 4, 115; H. Qi, S. Sharma, Z. Li, G. L. Snider, A. O. Orlov, C. S. Lent, T. P. Fehlner, *J. Am. Chem. Soc.* 2003, 125, 15250; C. S. Lent, B. Isaksen, M. Lieberman, *J. Am. Chem. Soc.* 2003, 125, 1056.

Tricyclic compounds such as carbazole derivatives can be used as bistable molecules for computing systems based on the QCA paradigm. A carbazole derivative is known to contain a ferrocenyl vinyl substituent, and specifically the compound of the following formula.

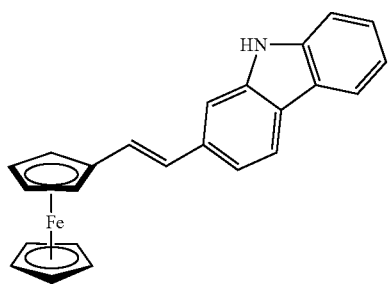

Such compound is known from Wang Xu-Chun et al., *Transition Metal Chemistry*, Vol. 32, No. 5, August 2007, pages 551-557.

BRIEF SUMMARY

According to various embodiments, new bistable compounds, useful as basic functional units for computing systems based on the QCA (Quantum Cellular Automata) paradigm, are described.

One embodiment provides compounds of the following formula (I)

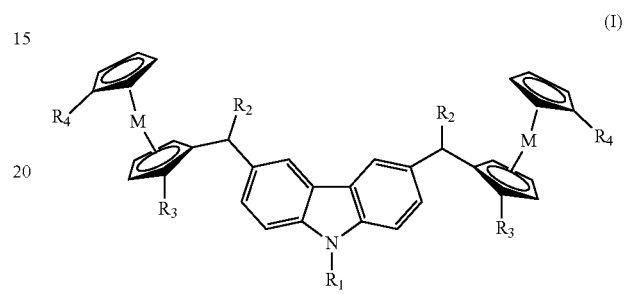

wherein:

each M is the same or different and independently Fe, Co, Ru, or Os;

each $R_1$ is the same or different and independently H, aryl, alkyl, aralkyl, $R_5$-alkyl, $R_5$-aryl, or $R_5$-aralkyl;

each $R_2$ is the same or different and independently aryl, alkyl, or heteroaryl;

each $R_3$ is the same or different and independently H, aryl, alkyl, I, $SR_6$, or $P(R_6)_2$;

each $R_4$ is the same or different and independently H, aryl, alkyl, I, $SR_6$, or $P(R_6)_2$;

$R_5$=I, Br, OH, SH, CN, $COOR_7$, CHO, SCN, $N_3$, $C_2$-$C_4$ alkenyl, $C_2$-$C_4$ alkynyl, or phenylvinyl;

$R_6$=phenyl, or cyclohexyl;

$R_7$=methyl, ethyl, or benzyl;

or enantiomers, diastereoisomers and salts thereof.

Other embodiments of the present disclosure further describe the method of making and using the compounds according to formula (I) as basic functional units for computing systems based on the QCA (Quantum Cellular Automata) paradigm.

A further embodiment provides a Quantum Cellular Automata (QCA) device comprising a basic functional unit that includes four quantum dots, wherein each quantum dot incorporates a compound of formula (I), as defined herein.

The present disclosure also regards the use of the compounds according to formula (I) as basic functional units for computing systems based on the QCA (Quantum Cellular Automata) paradigm.

DETAILED DESCRIPTION

Figure 1:
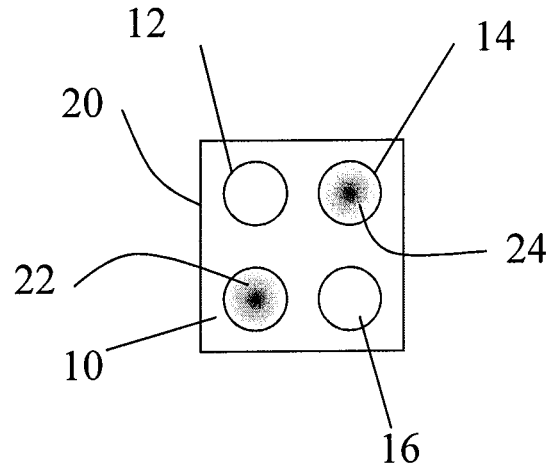
FIG. 1 represents a basic computational unit (cell)

Thus, one embodiment provides compounds of the following formula (I)

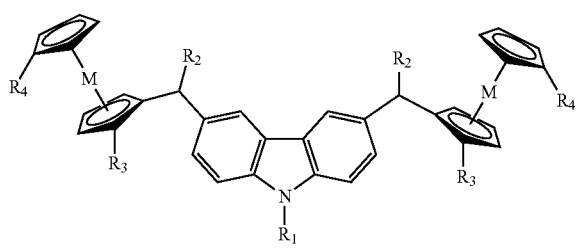

(I)

wherein:

each M is the same or different and independently Fe, Co, Ru, or Os;

each $R_1$ is the same or different and independently H, aryl, alkyl, aralkyl, $R_5$-alkyl, $R_5$-aryl, or $R_5$-aralkyl;

each $R_2$ is the same or different and independently aryl, alkyl, or heteroaryl;

each $R_3$ is the same or different and independently H, aryl, alkyl, I, $SR_6$, or $P(R_6)_2$;

each $R_4$ is the same or different and independently H, aryl, alkyl, I, $SR_6$, or $P(R_6)_2$;

$R_5$=I, Br, OH, SH, CN, $COOR_7$, CHO, SCN, $N_3$, $C_2$-$C_4$ alkenyl, $C_2$-$C_4$ alkynyl, or phenylvinyl;

$R_6$=phenyl, or cyclohexyl;

$R_7$=methyl, ethyl, or benzyl;

or enantiomers, diastereoisomers and salts thereof.

As used herein, "alkyl" refers to a straight (i.e., unbranched) or branched hydrocarbon chain radical comprising carbon and hydrogen atoms, containing no unsaturation, having from one to twenty carbon atoms (i.e., $C_1$-$C_{20}$ alkyl). In certain embodiments, an alkyl may comprise two to fourteen carbon atoms (i.e., $C_1$-$C_{14}$ alkyl). In other embodiments, an alkyl may comprise one to three carbon atoms (i.e., $C_1$-$C_3$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Alkyl can be further substituted at one or more carbons with, for example, I, Br, OH, SH, CN, $COOR_7$, CHO, SCN, $N_3$, $C_2$-$C_4$ alkenyl, $C_2$-$C_4$ alkynyl, or phenylvinyl.

"Alkenyl" refers to a straight or branched hydrocarbon chain radical group comprising carbon and hydrogen atoms, containing at least one double bond, and having from two to twelve carbon atoms. In certain embodiments, an alkenyl may comprise two to eight carbon atoms. In other embodiments, an alkenyl may comprise two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

"Alkynyl" refers to a straight or branched hydrocarbon chain radical group comprising carbon and hydrogen atoms, containing at least one triple bond, having from two to twelve carbon atoms. In certain embodiments, an alkynyl may comprise two to eight carbon atoms. In other embodiments, an alkynyl has two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like.

"Aryl" or "Ar" refers to a radical derived from an aromatic monocyclic or multi-cyclic hydrocarbon ring system by removing a hydrogen atom from a ring carbon atom. The aromatic monocyclic or multi-cyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as $C_6$ aryl (i.e., phenyl), $C_9$ aryl (e.g., fluorenyl), and $C_{10}$ aryl (e.g., naphthyl). Aryl can be further substituted at one or more carbons with, for example, I, Br, OH, SH, CN, $COOR_7$, CHO, SCN, $N_3$, $C_2$-$C_4$ alkenyl, $C_2$-$C_4$ alkynyl, or phenylvinyl.

"Aralkyl" refers to an alkyl (as defined herein) substituted with an aryl group, for example, benzyl, diphenylmethyl and the like. Aralkyl can be further substituted at one or more carbons of the aryl or the alkyl portion with, for example, I, Br, OH, SH, CN, $COOR_7$, CHO, SCN, $N_3$, $C_2$-$C_4$ alkenyl, $C_2$-$C_4$ alkynyl, or phenylvinyl.

In certain embodiments, the aryl groups are $C_6$-$C_{10}$ aryl groups, the alkyl groups are $C_1$-$C_{14}$ alkyl groups, the aralkyl groups are $C_6$-$C_{10}$ aryl$C_1$-$C_8$ alkyl groups.

As used herein, the heteroaryl groups are selected from 3-7 membered aromatic rings, containing at least one heteroatom selected from O, N and S. In certain embodiments, the heteroaryl groups are selected from 5-6 membered aromatic rings containing at least one heteroatom selected from O, N and S. Exemplary heteroaryl groups are, without limitation, pyrrolyl, thienyl and furyl.

Certain embodiments describe the compounds of formula (I) in which $R_2$ is selected from the group comprising methyl, ethyl, allyl, phenyl and benzyl.

In one embodiment, M is Fe.

Further embodiments provide the compounds of formula (I) in which $R_3$ and $R_4$ are H, $R_2$ is methyl and $R_1$ is $R_5$—$C_6$-$C_{14}$ alkyl (i.e., $C_6$-$C_{14}$ alkyl substituted with one or more substituents selected from I, Br, OH, SH, CN, $COOR_7$, CHO, SCN, $N_3$, $C_2$-$C_4$ alkenyl, $C_2$-$C_4$ alkynyl or phenylvinyl).

Certain embodiments provide the following compounds:
9-benzyl-3,6-bis(1-ethylferrocene)-9H-carbazole;
3,6-bis(1-ethylferrocene)-9-(6-iodohexyl)-9H-carbazole;
S-6-[3,6-bis(1-ethylferrocene)-9H-carbazol-9-yl]-6-hexylethanethioate;
3,6-bis(1-ethylferrocene)-9H-carbazole.

In other embodiments, the present disclosure describes a process for preparing compounds of formula (I), which comprises the step of reacting the compound of formula (II)

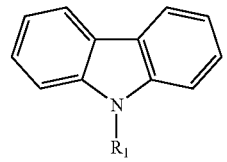

(II)

wherein $R_1$ has the same meanings reported for formula (I), except for the possible presence of protecting groups, with a compound of formula (III)

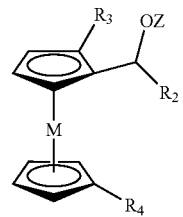

(III)

wherein M, $R_2$, $R_3$ and $R_4$ have the same meanings reported for the compounds of formula (I) and Z is H or $R_8CO$—, where $R_8$ is a $C_1$-$C_6$alkyl, preferably methyl, in the presence of a Lewis acid.

The molar ratio between the compound of formula (III) and the compound of formula (II) is at least equal to 2 and is typically between 2.1 and 2.5, for example, about 2.2.

As Lewis acid, at least one of the following compounds $InBr_3$, $Bi(OTf)_3$, $Al(OTf)_3$, $Zn(OTf)_2$, $BF_3$ and $BF_3(Et_2O)$ can be used, among others. The Lewis acid is used in a substantially equimolar quantity with respect to compound (II), typically a molar ratio varying from 1.0 to 1.1. In one embodiment, $Bi(OTf)_3$ is used.

The reaction is run at a temperature between about 0° C. and 50° C., typically at room temperature (20°-25° C.) in an organic solvent. The solvent is, for example, an aprotic organic solvent that is non-polar or has little polarity, such as methylene chloride.

The compounds according to the present disclosure can be prepared according to the following reaction scheme (A).

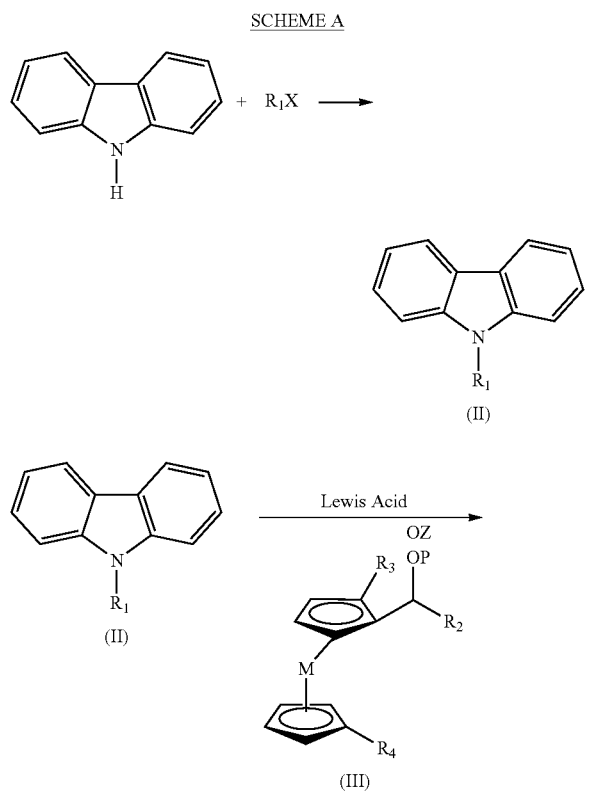

The synthesis of the compounds according to the present disclosure starts from carbazole, which is first alkylated on the nitrogen by a $R_1X$ compound, in which X is a leaving group, which can be chosen from the leaving groups commonly used for nucleophilic substitutions, such as halogens, in particular Cl, Br and I, —$OSO_2R'$ (where R' is an optionally fluorinated alkyl, such as for example $CF_3$, $C_4F_9$), —$OSO_2Ar$, where Ar is an aryl, in particular a tolyl group, etc.

The reaction is generally run in the presence of a strong base, such as alkali hydrides, in particular NaH, $NaNH_2$, alkali hydroxides etc.

The compound of formula (II) obtained via reaction between carbazole and $R_1X$ is subsequently subjected to a Friedel-Crafts reaction with the metallocene derivative (III), in the presence of a Lewis acid.

The Friedel-Crafts reaction can occur on both the positions 3 and 6 (i.e., di-substitution) of the carbazole or only on the position 3 (i.e., mono-substitution) depending on the stoichiometric ratio between the reagents and the employed experimental conditions. In order to provide bistable molecules adapted for use as basic functional units for computing systems based on the QCA paradigm, the most suitable experimental conditions were sought for obtaining compounds that are di-substituted on the carbazole moiety, because the presence of two non-conjugated metallocene groups in close proximity confers the desired properties to the molecule.

It was experimentally found that the best yields of disubstituted compound are obtained by using 2 to 2.5 equivalents of metallocene compound (III) per equivalent of compound (II) and in particular by using about 2.2 equivalents of metallocene compounds (III) per equivalent of compound (II).

By using a greater excess of metallocene compound (III), the yields do not increase and by-products are formed, including a compound deriving from the binding of the metallocene compound, not only in the positions 3 and 6 but also in position 1 of the carbazole.

As stated above, the Lewis acids usable in the Friedel-Craft reaction described above can be selected, for example, among $InBr_3$, $Bi(OTf)_3$, $Al(OTf)_3$, $Zn(OTf)_2$, $BF_3$ and $BF_3(Et_2O)$, with $Bi(OTf)_3$ leading to the highest yields. The Lewis acid is used in a substantially equimolar quantity with respect to the compound (II), typically in a molar ratio varying from 1.0 to 1.1.

If the reaction is run by using an enantiomerically enriched metallocene compound, the Friedel-Crafts reaction occurs with configuration retention and without racemization, as confirmed by the following reaction.

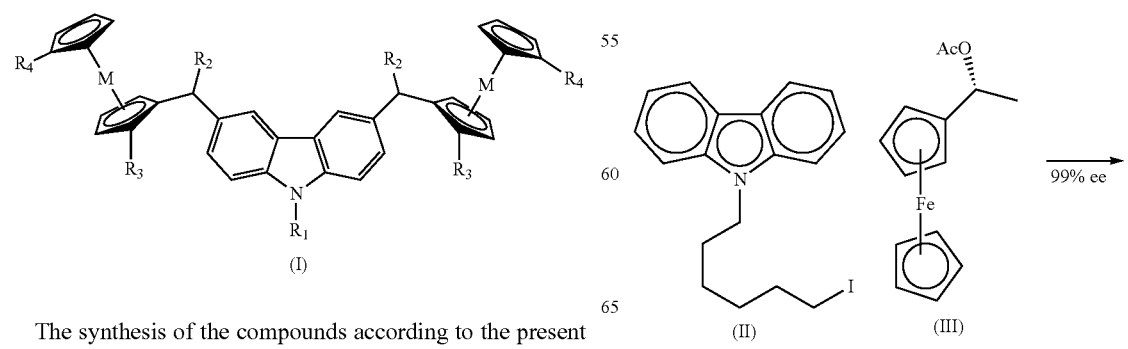

7
-continued

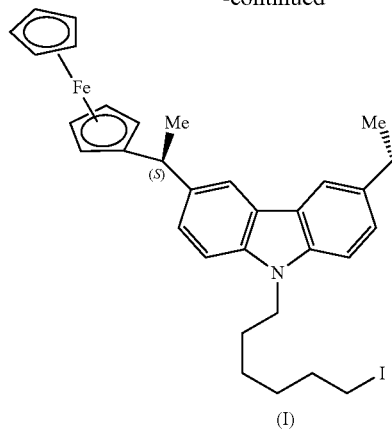

(I)

The reaction was run by using as catalyst Bi(OTf)$_3$ in a molar ratio of 1.1 with respect to the carbazole derivative (II), in dichloromethane, at room temperature. The molar ratio between compound (III) and compound (II) was 2.2.

The compound (I) obtained at the end of the reaction, with a yield of 46%, was a single diastereoisomer.

The complete lack of racemization in the Friedel-Crafts reactions is important, since it allows the optically active compounds obtained according to the present disclosure to transfer chiral properties to the surfaces on which they are applied.

The present disclosure describes the various embodiments in further detail by making reference to the attached figures and to several illustrative and non-limiting examples provided below.

Example 1

Preparation of 9-benzyl-3,6-bis(1-ethylferrocene)-9H-carbazole 9-benzyl-carbazole

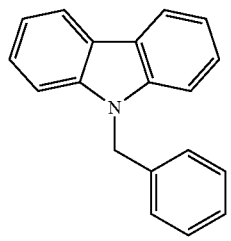 [SMILES: c1ccc(Cn2c3ccccc3c3ccccc32)cc1]

To a mixture of carbazole (0.87 g, 5 mmoles) in tetrahydrofuran (THF), NaH (0.24 g, 10 mmoles) was slowly added. The mixture was stirred for 1 hour, obtaining a solution. Benzyl bromide (0.89 ml, 7.5 mmoles) was then added dropwise, and the reaction mixture was stirred for 5 hours at room temperature. The reaction was quenched with ice water and THF was evaporated under reduced pressure. The mixture was extracted with ethyl ether (3×5 mL) and the organic phases were collected and combined, dried over MgSO$_4$ and evaporated under reduced pressure. The solid obtained was triturated with n-hexane (10 mL), filtered and used without further purification. The compound obtained is a white solid with melting point of 123° C. and R$_f$=0.44 in cyclohexane/dichloromethane 4/1.

1H-NMR (CDCl$_3$, 300 MHz) δ: 8.14 (d, 2H, J=7.5 Hz); 7.74-7.14 (m, 11H); 5.54 (s, 2H).

8

9-benzyl-3,6-bis(1-ethylferrocene)-9H-carbazole

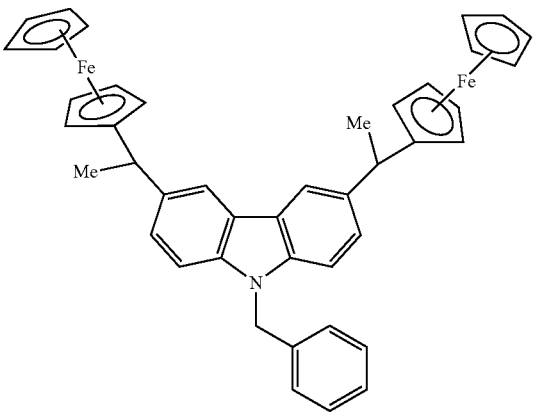

To a solution of 9-benzylcarbazole (0.021 g, 0.081 mmoles) in dichloromethane (1 ml), BF$_3$(Et$_2$O) (0.030 mL, 0.22 mmoles) was added at room temperature. The solution was carefully degassed through freezing-pump cycle and then a solution of ferrocene ethanol (0.05 g, 0.22 mmoles) in dichloromethane (1 mL) was added in 10 minutes at room temperature. After the addition of the ferrocene ethanol, the reaction was quenched with water and the dichloromethane was evaporated under reduced pressure. The mixture was extracted with ethyl ether (3×5 mL) and the organic phases were collected and combined, dried over Na$_2$SO$_4$ and evaporated under reduced pressure. The obtained crude product was purified by chromatography (from hexane to hexane: CH$_2$Cl$_2$ 5:1). Yield: 24%. R$_f$=0.27 (cyclohexane/dichloromethane 4/1)

1H-NMR (CDCl$_3$, 200 MHz) δ: 7.86 (s, 2H); 7.27-7.20 (m, 9H); 5.41 (s, 2H); 4.26-4.04 (m, 20H); 1.67 (d, 6H, J=7.2 Hz).

ESI MS: rt: 42.05 min; m/z: 378, 132.2.1, 105.2.

Example 2

Preparation of 3,6-bis(1-ethylferrocene)-9-(6-iodohexyl)-9H-carbazole 9-(6-iodohexyl)-9H-carbazole

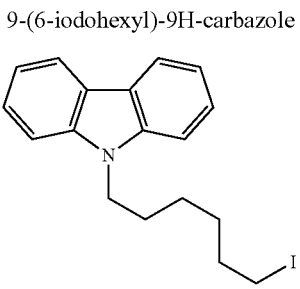

To a mixture of carbazole (0.5 g, 2.99 mmoles) in THF (6 mL), NaH (0.25 g, 6 mmoles) was slowly added. The mixture was stirred for 1 hour giving a solution. The resulting solution was introduced under nitrogen in a dropping funnel and slowly added in 10 minutes to a solution of 1,6-diiodo hexane (3 ml, 18 mmoles) in THF (2 mL). The reaction mixture stirred for 2 hours at room temperature, it was quenched with water and ice and THF was evaporated under reduced pressure. The mixture was extracted with ethyl ether (3×5 mL) and the organic phases were collected and combined, dried over Na$_2$SO$_4$ and evaporated under reduced pressure. The crude product was purified by chromatography (from n-hexane to n-hexane:CH$_2$Cl$_2$ 10:1). Yield: 83%. R$_f$=0.55 (cyclohexane/dichloromethane 3/1).

1H-NMR (CDCl$_3$, 300 MHz) δ: 8.00 (d, 2H, J=7.8 Hz); 7.35 (dt, 2H, J=6.9, 1.2 Hz); 7.25 (d, 2H, J=8.4 Hz); 7.12 (dt, 2H, J=8.1, 1.2 Hz); 4.11 (t, 2H, J=6.9 Hz); 3.02 (t, 2H, J=6.9 Hz); 2.96 (t, 2H, J=6.9 Hz); 1.72-1.54 (m, 3H); 1.39-1.18 (m, 3H).

ESI MS: rt: 16.03 min; m/z: 378, 132.2.1, 105.2.

3,6-bis(1-ethylferrocene)-9-(6-iodohexyl)-9H-carbazole

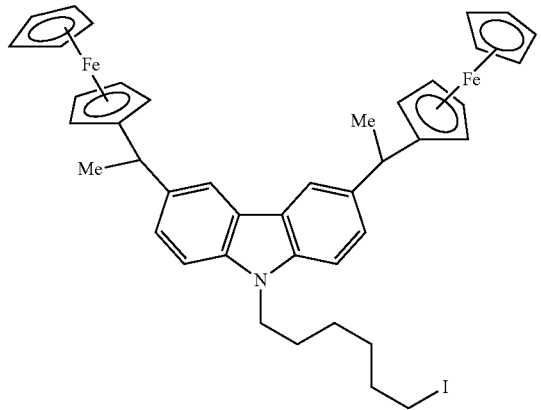

To a solution of 9-(6-iodohexyl)-9H-carbazole (0.02 g, 0.0318 mmoles) in dichloromethane (1 ml), ferroceneacetate (0.189 g, 0.692 mmoles) was added and subsequently Bi(OTf)$_3$ (0.021 g, 0.033 mmoles) was added at room temperature. The mixture was stirred at room temperature for 3 hours, after which the reaction was quenched with water and dichloromethane. The mixture was extracted with dichloromethane (3×5 mL) and the organic phases were collected and combined, dried over Na$_2$SO$_4$ and evaporated under reduced pressure. The crude product was purified by chromatography (from cyclohexane/dichloromethane 20:1 to cyclohexane/dichloromethane 9:2) Yield: 46%. R$_f$=0.29 (cyclohexane/dichloromethane 3:1). Yellow solid, melting point: 60-69° C.

1H-NMR (CDCl$_3$, 200 MHz) δ: 7.83 (s, 2H); 7.27-7.23 (m, 4H); 4.25-4.02 (m, 20H); 3.13 (t, 2H, J=7 Hz); 1.89-1.38 (m, 10H); 1.68 (d, 6H, J=7.4 Hz).

ESI MS: rt: 88.87 min; m/z: 802.1, 801.2, 799.1, 400.5.

Example 3

S-6-[3,6-bis(1-ethylferrocene)-9H-carbazol-9-yl]-6-hexylethanethioate

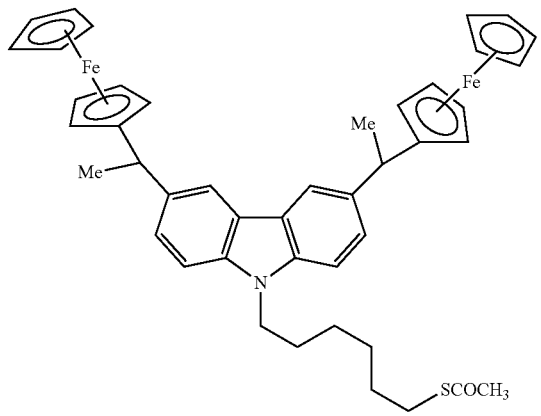

The compound obtained in the preceding example (3,6-bis(1-ethylferrocene)-9-(6-iodohexyl)-9H-carbazole) (0.42 g, 0.56 mmoles) was dissolved in DMF (2 ml) and then potassium thioacetate (0.072 g, 0.62 mmoles) was added thereto. The mixture was stirred at room temperature overnight. The reaction was quenched by adding dichloromethane/acidic water (1:1 with 1 M HCl, 10 mL) to the reaction mixture, which was then washed twice with acidic water. The organic phases were then dried over Na$_2$SO$_4$ and evaporated under reduced pressure. The crude product was used without any further purification. Quantitative yield. R$_f$=0.25 (cyclohexane/dichloromethane 3/1); yellow oil.

1H-NMR (CDCl$_3$, 300 MHz) δ: 7.85 (s, 2H); 7.27-7.22 (m, 4H); 4.27-3.94 (m, 20H); 2.84 (t, 2H, J=6.9 Hz); 2.32 (s, 3H); 1.82-1.38 (m, 8H); 1.70 (d, 6H, J=7.8 Hz); 0.92 (t, 2H, J=7.2 Hz).

ESI MS: no ionization.

Example 4

6-[3,6-bis(1-ethylferrocene)-9H-carbazole-9-yl]-6-hexane-1-thiol

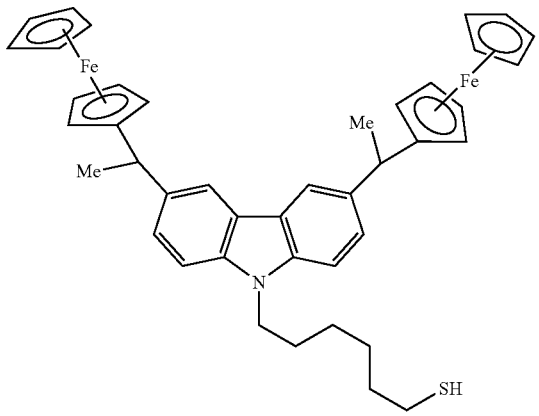

0.019 g (0.0025 mmoles) of S-6-[3,6-bis(1-ethylferrocene)-9H-carbazole-9-yl]hexylethanethioate were dissolved in isopropyl alcohol/THF/H$_2$O 2.5:6:1.5 and subsequently the mixture was carefully degassed through a freezing/thawing cycle. Solid KOH (0.098 g, 1.75 mmoles) was then added and the mixture was stirred at 60° C. for 3 hours, after which the reaction was quenched with 1M HCl until pH was neutral. The mixture was extracted with ethyl ether (3×5 mL) and the organic phases were collected and combined, dried over Na$_2$SO$_4$ and evaporated under reduced pressure. The crude product was washed with water and purified by chromatography (from cyclohexane:dichloromethane 3:1). Yield: 30%. R$_f$=0.26 (cyclohexane/dichloromethane 3/2). Yellow solid, melting point 65.5-87° C.

1H-NMR (CDCl$_3$, 200 MHz) δ: 7.83 (s, 2H); 7.27-7.22 (m, 4H); 4.25-3.98 (m, 20H); 2.55 (t, 2H, J=7.2 Hz); 2.32 (s, 2H); 1.89-0.8 (m, 10H); 1.68 (d, 6H, J=7 Hz).

ESI MS: no ionization.

Example 5

3,6-bis(1-ethylferrocene)-9H-carbazole

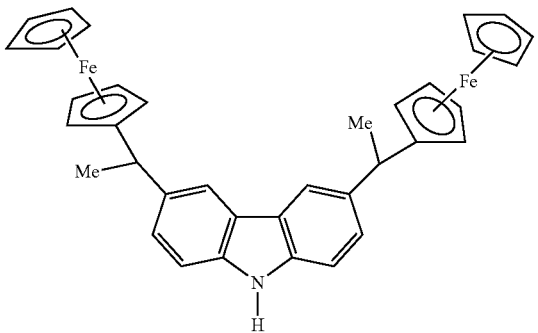

0.006 g (0.0088 mmoles) of 9-benzyl-3,6-bis(1-ethylferrocene)-9H-carbazole (obtained according to Example 3) were dissolved in DMSO/THF (1.5 ml: 0.46 ml) and subsequently potassium tert-butoxide (0.049 g, 0.44 mmoles) was added. Dried oxygen was insufflated into the reaction mixture until the starting compound was completely consumed. The reaction was quenched with water and then the mixture was extracted with ethyl ether (3×5 mL) and the organic phases were collected and combined, dried over $Na_2SO_4$ and evaporated under reduced pressure. The crude product was purified by chromatography (from cyclohexane/dichloromethane 2:1). Yield: 60%. $R_f$=0.23 (hexane/dichloromethane 2/1). Yellow solid, melting point 77-85° C.

1H-NMR (CDCl3.300 MHz) δ: 7.86-7.18 (m, 7H); 4.26 (brs, 2H); 4.16-4.02 (m, 20H); 1.67 (d, 6H, J=7.2 Hz).

ESI MS: rt: 27.55 min; m/z: 716.9, 593, 592.1, 591.0, 589.0.

As discussed above, the compound according to the present disclosure can be advantageously applied as a basic functional unit for computing systems based on the QCA (Quantum Cellular Automata) paradigm.

In FIG. 1, a basic computational unit or cell is schematically represented of one such computing system according to the classic QCA paradigm. In particular, such cell is composed of four quantum dots (10, 12, 14, 16, respectively) at the corners of a square 20, charges confined in such four-dots system allowing the internal tunneling between points. In FIG. 1, two of these quantum dots (10 and 14) are each filled with a spot (22 and 24, respectively) to indicate the localization thereon of an electric charge; the remaining two quantum dots (12 and 16) left white or empty, on the other hand, are not occupied with a charge in the represented moment. Nevertheless, it should be underlined that the four quantum dots of the cell of FIG. 1 are per se identical from the structural standpoint.

When quantum dots are made on a molecular scale, organometallic complexes are often selected in which each metal ion functions as a quantum dot. In fact, each metal ion can have two different oxidation states (and thus may or may not host one charge).

Nevertheless, the metal ion does not per se constitute the active charge of the quantum dot. Such active charge, in fact, can move from one metal ion to another inside a molecule, by using the ions themselves only as seats for the temporary confinement of such charge, obtained by means of a suitable process, for example by oxidation.

Advantageously, the compound according to the disclosure lends itself for achieving ordered configurations of quantum dots immobilized on a substrate, for example of square type like that illustrated for the cell of FIG. 1.

In addition, the compound according to the disclosure, by possessing two ions or quantum dots, can constitute an entire bistable electric cell, usable in variants of the QCA paradigm in which the Boolean logic value is coded from the position of the single charge (rather than from the occupied diagonal).

Figure 2:
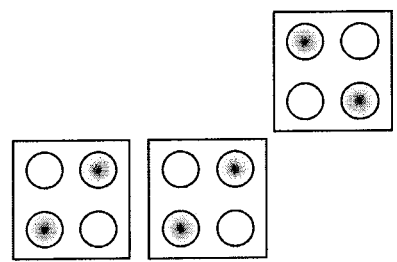
FIG. 2 represents the arrangement of the charges in three adjacent cells.

Analogously, in FIG. 2, the arrangement of the charges in three adjacent cells is illustrated. As already explained in relation to the prior art, such arrangement is selected so as to minimize the overall electrostatic energy and thus the Coulomb repulsion.

Figure 3:
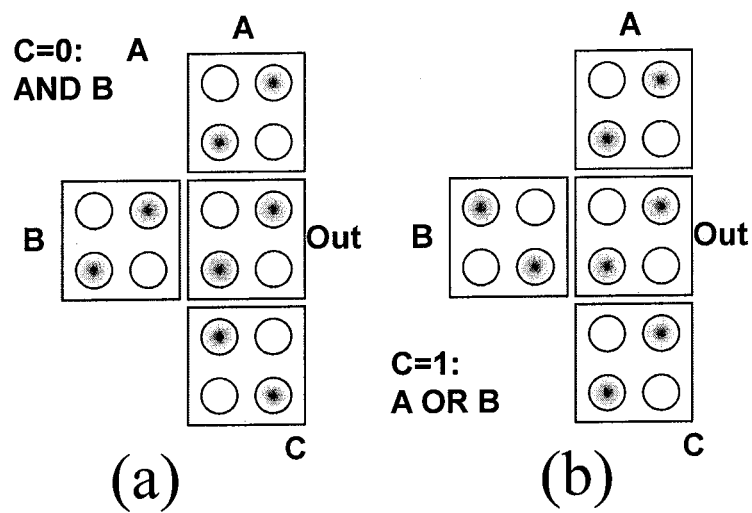
FIG. 3 illustrates the basic QCA computing gate or majority gate.

Finally, in FIG. 3, a logic gate or basic QCA computing gate is schematically illustrated, adapted to supply, on the output Out, the result of the functions AND (a) and OR (b) of the values present on the inputs A and B, simply by differently setting the flag C.

The various embodiments described above can be combined to provide further embodiments. All of the patents, patent application publications, patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound of formula (I)

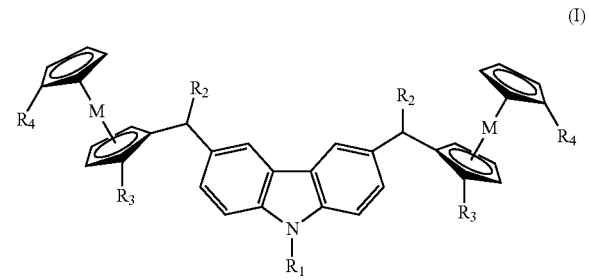

wherein:
each M is the same or different and independently Fe, Co, Ru, or Os;

each $R_1$ is the same or different and independently H, aryl, alkyl, aralkyl, $R_5$-alkyl, $R_5$-aryl, or $R_5$-aralkyl;

each $R_2$ is the same or different and independently aryl, alkyl, or heteroaryl;

each $R_3$ is the same or different and independently H, aryl, alkyl, I, $SR_6$, or $P(R_6)_2$;

each $R_4$ is the same or different and independently H, aryl, alkyl, I, $SR_6$, or $P(R_6)_2$;

$R_5$=I, Br, OH, SH, CN, $COOR_7$, CHO, SCN, $N_3$, $C_2$-$C_4$ alkenyl, $C_2$-$C_4$ alkynyl, or phenylvinyl;

$R_6$=phenyl, or cyclohexyl;

$R_7$=methyl, ethyl, or benzyl;

or enantiomers, diastereoisomers and salts thereof.

2. A compound according to claim 1, wherein M is Fe.

3. A compound according to claim 2, wherein
$R_1$=H, $C_6$-$C_{10}$ aryl, $C_1$-$C_{14}$ alkyl, $C_6$-$C_{10}$aryl$C_1$-$C_8$alkyl, $R_5$—$C_1$-$C_{14}$ alkyl, $R_5$—$C_6$-$C_{10}$ aryl, or $R_5$—$C_6$-$C_{10}$aryl$C_1$-$C_8$alkyl;
$R_2$=$C_6$-$C_{10}$aryl, $C_{1-14}$ alkyl, or heteroaryl;
$R_3$=H, $C_6$-$C_{10}$ aryl, $C_1$-$C_{14}$ alkyl, I, $SR_6$, or $P(R_6)_2$;
$R_4$=H, $C_6$-$C_{10}$ aryl, $C_1$-$C_{14}$ alkyl, I, $SR_6$, or $P(R_6)_2$;
$R_5$=I, Br, OH, SH, CN, $COOR_7$, CHO, SCN, $N_3$, $C_2$-$C_4$ alkenyl, $C_2$-$C_4$ alkynyl, or phenylvinyl;
$R_6$=phenyl, or cyclohexyl;
$R_7$=methyl, ethyl, or benzyl.

4. A compound according to claim 3, wherein $R_2$ is methyl, ethyl, allyl, phenyl or benzyl.

5. A compound according to claim 4, wherein $R_3$ and $R_4$ are H, $R_2$ is methyl and $R_1$ is $R_5$—$C_6$-$C_{14}$alkyl.

6. The compound according to claim 5 wherein $R_5$ is —SH or —I.

7. The compound according to claim 4 wherein $R_3$ and $R_4$ are H, $R_2$ is methyl and $R_1$ is benzyl.

8. A compound according to claim 1, having the following formula:
9-benzyl-3,6-bis(1-ethylferrocene)-9H-carbazole;
3,6-bis(1-ethylferrocene)-9-(6-iodohexyl)-9H-carbazole;
S-6-[3,6-bis(1-ethylferrocene)-9H-carbazol-9-yl]-6-hexylethanethioate; or
3,6-bis(1-ethylferrocene)-9H-carbazole.

9. A process for preparing a compound of Formula (I)

(I)

wherein:
each M is the same or different and independently Fe, Co, Ru, or Os;
each $R_1$ is the same or different and independently H, aryl, alkyl, aralkyl, $R_5$-alkyl, $R_5$-aryl, or $R_5$-aralkyl;
each $R_2$ is the same or different and independently aryl, alkyl, or heteroaryl;
each $R_3$ is the same or different and independently H, aryl, alkyl, I, $SR_6$, or $P(R_6)_2$;
each $R_4$ is the same or different and independently H, aryl, alkyl, I, $SR_6$, or $P(R_6)_2$;
$R_5$=I, Br, OH, SH, CN, $COOR_7$, CHO, SCN, $N_3$, $C_2$-$C_4$ alkenyl, $C_2$-$C_4$ alkynyl, or phenylvinyl;
$R_6$=phenyl, or cyclohexyl;

$R_7$=methyl, ethyl, or benzyl;
or enantiomers, diastereoisomers and salts thereof, comprising the step of reacting a compound of formula (II)

(II)

with a compound of formula (III)

(III)

wherein M, $R_1$, $R_2$, $R_3$ and $R_4$ are as defined for formula (I) and Z is H or $R_8CO$—, where $R_8$ is a $C_1$-$C_6$alkyl, in the presence of a Lewis acid.

10. A process according to claim 9, in which the molar ratio between the compound of formula (III) and the compound of formula (II) is 2 or higher than 2.

11. A process according to claim 9, in which the molar ratio between the compound of formula (III) and the compound of formula (II) is between about 2.1 and 2.5, preferably about 2.2.

12. A process according to claim 9, in which said Lewis acid is selected among the group comprising $InBr_3$, $Bi(OTf)_3$, $Al(OTf)_3$, $Zn(OTf)_2$, $BF_3$ or $BF_3(Et_2O)$.

13. A process according to claim 9, in which said Lewis acid is used in a molar ratio between about 1.0 and 1.1, with respect to the compound of formula (I).

14. A process according to claim 9, in which said Lewis acid is $Bi(OTf)_3$.

15. A process according to claim 9, in which said reaction is run at a temperature between about 0° C. and 50° C., preferably at room temperature (20° C.-25° C.), in an organic solvent.

16. A Quantum Cellular Automata (QCA) device comprising a basic functional unit that includes four quantum dots, wherein each quantum dot incorporates a compound of formula (I):

(I)

wherein:
- each M is the same or different and independently Fe, Co, Ru, or Os;
- each $R_1$ is the same or different and independently H, aryl, alkyl, aralkyl, $R_5$-alkyl, $R_5$-aryl, or $R_5$-aralkyl;
- each $R_2$ is the same or different and independently aryl, alkyl, or heteroaryl;
- each $R_3$ is the same or different and independently H, aryl, alkyl, I, $SR_6$, or $P(R_6)_2$;
- each $R_4$ is the same or different and independently H, aryl, alkyl, I, $SR_6$, or $P(R_6)_2$;
- $R_5$=I, Br, OH, SH, CN, $COOR_S$, CHO, SCN, $N_3$, $C_2$-$C_4$ alkenyl, $C_2$-$C_4$ alkynyl, or phenylvinyl;
- $R_6$=phenyl, or cyclohexyl;
- $R_7$=methyl, ethyl, or benzyl;
- or enantiomers, diastereoisomers and salts thereof.

17. The QCA device of claim 16 wherein the compounds of formula (I) in respective quantum dots are in the same or different oxidative states.

18. The QCA device of claim 16 wherein the four quantum dots within each basic functional unit are arranged as four corners of a square.

19. The QCA device of claim 18 wherein electrons of the compound of formula (I) are localized along a diagonal of the basic functional unit.

20. The QCA device of claim 18 wherein the compound of formula (I) is one or more of the following:
- 9-benzyl-3,6-bis(1-ethylferrocene)-9H-carbazole;
- 3,6-bis(1-ethylferrocene)-9-(6-iodohexyl)-9H-carbazole;
- S-6-[3,6-bis(1-ethylferrocene)-9H-carbazol-9-yl]-6-hexylethanethioate; and
- 3,6-bis(1-ethylferrocene)-9H-carbazole.

* * * * *